United States Patent [19]

Hicks

[11] 4,273,922
[45] Jun. 16, 1981

[54] KETOSE SUGARS FROM ALDOSE SUGARS

[75] Inventor: Kevin B. Hicks, Glenside, Pa.

[73] Assignee: The United States of America as represented by the Secretary of Agriculture, Washington, D.C.

[21] Appl. No.: 132,595

[22] Filed: Mar. 21, 1980

[51] Int. Cl.$^3$ .......................... C07H 3/02; C07H 3/04
[52] U.S. Cl. .......................................... 536/1; 127/30; 127/46 R
[58] Field of Search .............. 127/30, 31, 46 R, 46 A, 127/42; 536/1

[56] References Cited

U.S. PATENT DOCUMENTS

| | | | |
|---|---|---|---|
| 3,505,309 | 4/1970 | Carubelli . | |
| 3,514,327 | 5/1970 | Parrish | 127/30 X |
| 3,546,206 | 12/1970 | Guth | 127/30 X |
| 3,707,534 | 12/1972 | Nitsch . | |
| 3,816,174 | 6/1974 | Nagasawa | 127/30 X |
| 3,875,140 | 4/1975 | Barker | 127/46 A |

OTHER PUBLICATIONS

J. F. Mendicino, J.A.C.S., 82, 4975–4979 (1960).
E. M. Montgomery et al., J.A.C.S., 52, 2101–2106 (1930).
L. Hough et al., J. Chem. Soc.; (London), 2005–2009 (1953).
F. W. Parrish et al., J. Food Sci., 44, 813–816 (1979).
Chemical Abstracts, 83:97847f (1975).
Chemical Abstracts, 83:179507j (1975).
Chemical Abstracts, 80:122660n (1974).
Chemical Abstracts, 79:126744v (1973).
Chemical Abstracts, 78:113041t (1973).

Primary Examiner—Sidney Marantz
Attorney, Agent, or Firm—M. Howard Silverstein; William E. Scott; David G. McConnell

[57] ABSTRACT

Ketose sugars are prepared in high yield by reacting an aldose sugar and boric acid in aqueous medium in the presence of a tertiary or quaternary amine.

5 Claims, No Drawings

KETOSE SUGARS FROM ALDOSE SUGARS

BACKGROUND OF THE INVENTION

1. Field of the Invention

This invention relates to a process for making ketose sugars and more specifically to a process for converting in high yield aldose sugars to ketose sugars.

2. Description of the Art

Presently available methods for making ketose sugars are not very satisfactory. Some methods produce ketose sugars in low yields with many degradation products. This presents the problem of isolating the ketose sugar from unreacted starting materials, alkaline degradation products, and in some cases metal ions. Other methods of producing ketose sugars produce relatively high product yield but it is very difficult to separate the product from the isomerization reagents.

SUMMARY OF THE INVENTION

An object of this invention is to provide a method of making ketose sugars from aldose sugars.

Another object is to provide a method of making ketose sugars in high yield.

Still another object is to provide a method of making ketose sugars in which the reagent and catalyst may be completely recycled and be available for subsequent reaction.

A further object is to provide a method of making ketose sugars in which the reaction product contains very few degration products.

A still further object is to provide a method in which the degradation products are easily removed by ion exchange.

Another further object is to provide a method of making ketose sugars which eliminates much of the need for disposal of reagent and catalyst and its resultant environmental pollution.

In general, according to this invention the above objects are accomplished by a process wherein an aldose sugar and boric acid are reacted in aqueous medium in the presence of a tertiary or quaternary amine catalyst.

DETAILED DESCRIPTION OF THE INVENTION

Ketose sugars are important both economically and academically. For example, fructose has a sweetening value equal to that of sucrose but only half the calories. At present, in spite of the fact that glucose is a readily available product of the corn refining industry, there is no industrial chemical process for converting glucose to fructose. Although lactulose is a commercially valuable product in the pharmaceutical industry and has much potential as a non-caloric substitute for sucrose in the food industry, there is no available chemical process to prepare it economically in commercial quantity. Tagatose, which is of academic importance at present, is not obtained easily by conventional procedures.

This invention provides a much needed process for converting in high yield aldose sugars such as glucose, galactose and lactose to the corresponding ketose sugars, fructose, tagatose, and lactulose, respectively. The conversion is effected by the isomerizing action of a reagent consisting of a tertiary or quaternary amine and boric acid. The aldose sugar is reacted in aqueous solution at a carbohydrate concentration of about 5 to 36% w/v and a boric acid concentration of about 0.89 to 6.4% w/v, respectively, (the molar ratio of carbohydrate to boric acid is 1:1) in the presence of a tertiary or quaternary amine catalyst a pH range of about 9 to 11 and at a temperature range of from about 38° to 70° C. to yield the desired ketose sugar. Unlike some known processes, the process is accompanied by little or no alkaline degradation of the sugars. Tertiary amines such as 1,4-dimethylpiperazine, N-methyl-piperidine, N,N,N',N'-tetramethylethylenediamine, and triethylamine and quaternary amines such as N-benzyl, N,N,N-trimethylammonium methoxide are examples of catalysts suitable for use in the process of the invention.

When the catalyst is triethylamine, both the triethylamine and the boric acid can be reclaimed from the reaction and used in a subsequent reaction. When a catalyst other than triethylamine is used, boric acid can be reclaimed but the catalyst, which is removed with ion exchange resins, cannot be recovered easily. However, regardless of which amine is used as a catalyst, the resultant solution, after removal of catalyst and boric acid, contains a high yield of ketose sugar accompanied by little or no degradative by- or starting products.

The pH and temperature of the reactants have a decided effect on the rate at which the reaction proceeds. The effect of pH on the rate at which aldose sugar is converted to ketose sugar is illustrated in Table 1 which shows the conversion of lactose to lactulose in the presence of triethylamine and boric acid. The reaction was run for 96 hours at 40° C. The yield of lactulose and monosaccharides (as D-galactose and D-tagatose) were measured by quantitative high pressure liquid chromatography (HPLC). The effect of temperature on the rate of conversion is seen by comparing the yield of lactulose (83%) at pH 11.0 in Table 1 with the yield in Table 2 (87%) when lactose was converted to lactulose in the presence of triethylamine and boric acid. In making this comparison consideration must be given to the fact that the yield shown in Table 2 was obtained after only 4 hours reaction at 70° C. Table 2 also illustrates the effect of the type of tertiary amine on the product yield. The yields were measured as described above for Table 1.

Although the process can be operated over a fairly widespread range of temperatures and pH values, the preferred ranges are temperatures of from about 38° C. to about 70° C. and pH values of from about 9.0 to about 11.0. Maximum yield is obtained in the shortest time by increasing the temperature at which the reaction is run as illustrated above in the conversion of lactose to lactulose in the presence of triethylamine and boric acid at a pH of 11.0 and a temperature of 70° C. The yield of 87% after 4 hours reaction time is slightly greater than the 83% yield obtained after 96 hours reaction time at 40° and pH 11.0. The pH at which reaction is run also effects the rate; the reaction rate is accelerated at the higher pH value. With respect to operating conditions, the process is somewhat flexible because maximum yields can be obtained by varying the time of reaction at any given temperature and pH value. If energy conservation is a factor in operating the process, maximum yield can still be obtained by operating at lower temperatures for a longer period of time.

Since the process occurs in a sealed vessel the system reaches an equilibrium pressure which may be greater than atmospheric. However, the pressure is not critical to obtain maximum yield and it is not necessary to make adjustments to control the pressure. If the pressure exceeds what is considered to be a safe level, the vessel can be vented to relieve excess pressure with no effect on product yield. The preferable ratio of carbohydrate to boric acid is 1:1 on a molar basis.

The invention is operable with any aldose sugar which can be isomerized by the action of a base to yield a ketose sugar that can be complexed and stabilized by boric acid. Any tertiary or quaternary amine that is sufficiently water soluble and basic enough to adjust the pH of the reaction solution to about 9.0 to 11.0 may be used in the process. If a tertiary or quaternary amine meets the above requirements and has a boiling point below that of water and does not form azeotropes with water, it can be reclaimed from the solution by distillation and reused in subsequent reactions. This obviates the need for cation exchange resins to remove the amine from solution.

Two examples in which reclaimed reagents were reused or recycled after having been used previously to convert lactose to lactulose with triethylamine and boric acid are shown in Table 3. In both examples, the pH was determined at ambient room temperature (about 20° to 25° C.), the yields were determined by quantitative HPLC, and the monosaccharides were expressed as D-galactose and D-tagatose. In sample 1 each cycle was run for two hours at 70° C. and in sample 2 each cycle was run for four hours at 70° C.

As previously noted with reference to Table 2, several tertiary amines were found to be effective catalysts in the process of the invention and provide yields of lactulose ranging from 21% to 87%. In all cases, lactose was the only sugar present other than lactulose and two monosaccharides having HPLC retention times identical to D-tagatose and D-galactose. In addition to the tertiary amines, a quaternary amine salt, N-benzyl, N,N,N-trimethyl ammonium methoxide, when reacted with lactose at pH 10.9 for three hours at 70° C. produced an 83% yield of lactulose.

The process of the invention is illustrated in the following examples wherein, as in all examples heretofore cited, sugars were quantitatively determined by HPLC on a $\mu$ Bondapak/Carbohydrate column eluted at 1.0 ml per minute with acetonitrile/water at a 77:23, w/w, ratio, the pH values determined at ambient room temperature (about 20°–25° C.), and the monosaccharides determined as D-galactose and D-tagatose. The HPLC method used is the same as that described on pages 214–215 of Carbohydrate Research 70 (1979) 209–216. The $\mu$ Bondapak/Carbohydrate column is a high efficiency liquid chromatography column packing material designed specifically for sugar separations. Other columns such as Zorbax $NH_2$ may also be used.

EXAMPLE 1

Four samples, each of which contained 5.0 gm $\alpha$-D-lactose monohydrate (14 mmol), 0.89 gm boric acid (14 mmol) and 100 ml water, were adjusted to pH 9.0, 10.0, 10.5, and 11.0 with 1.45 ml, 2.4 ml, 3.2 ml, and 6.0 ml of triethylamine, respectively. Each of the pH adjusted samples was warmed at 40° C. in a water bath for 96 hours. The triethylamine was then removed by passing the reacted samples individually through a separate column (1×12 cm) of IR 120-H+ resin. Any strong acid, as sulfonic acid, type of exchange resin is suitable in the invention. Boric acid was then removed as the methyl ester by evaporating each of the remaining samples to dryness under reduced pressure (about 15 mm), adding 40 ml of absolute methanol to each and reconcentrating and repeating the process three times. The final residue of each sample was dissolved in 10.0 ml of water and 10.0 ml acetonitrile and analyzed by quantitative HPLC. The results are shown in Table 1.

EXAMPLE 2

Four samples, each of which contained 5.0 gm $\alpha$-D-lactose monohydrate (14 mmol), 0.89 gm boric acid (14 mmol) and 100 ml water were prepared and the pH of each was adjusted with a different amine. The first was adjusted to pH 9.5 with 1,4-dimethylpiperazine; the second to pH 10.8 with N-methyl-piperidine; the third to pH 9.7 with N,N,N',N'-tetramethylethylenediamine; and the fourth to pH 11.0 with triethylamine. The basicity and water solubility of the amines used to adjust the pH of the first three samples is not sufficient to raise the pH values higher than the adjusted values shown above. Each of the samples was then reacted at 70° C., the first three for three hours and the fourth for four hours. The solutions were then treated as described in Example 1 to determine the extent to which the aldose sugars were converted to ketose sugars. The results are shown in Table 2.

EXAMPLE 3

A sample containing 5.0 gm of $\alpha$-D-lactose monohydrate and 0.89 gm of boric acid in 100 ml of water was adjusted to a pH of 11.0 with 6.0 ml of triethylamine and then reacted at 70° C. for 2 hours (cycle 1). The reacted sample was evaporated to dryness under reduced pressure (about 15 mm) at 35° C. and the distillate, containing triethylamine and water (distillate A) was collected in a cold trap (dry ice/acetone). The sample was then treated with anhydrous methanol to remove boric acid as described in Example 1. The methanol/methylborate distillate from this treatment was then mixed with an equal volume of water and evaporated to dryness under reduced pressure (about 15 mm) at 35° C. to yield a residue of crystalline boric acid. Distillate A was then mixed with the reclaimed boric acid, 5 gm of $\alpha$-D-lactose monohydrate added and the mixture reacted at 70° C. for 2 hours (cycle 2). The results are shown in Table 3 as Sample 1.

A second 5.0 gm sample of $\alpha$-D-lactose was treated the same as Sample 1 except the reaction time for each cycle was extended to 4 hours. The results are shown in Table 3 as Sample 2.

EXAMPLE 4

Five grams of $\alpha$-D-lactose were reacted with boric acid and triethylamine in aqueous medium for 4 hours at 70° C. and the amine and boric acid removed as described above to obtain 4.8 gm of dry residue. The residue was dissolved in 5 gm of absolute methanol, incubated with gentle motion at 40° C. to yield 6.0 gm of wet crystals which were isolated on a filter, washed with cold methanol and dried in a vacuum desiccator. The dried crystalline product weighed 2.9 gm, was slightly hygroscopic, had a m.p. of 155°–160° C., and was 90% pure lactulose by HPLC. Recrystallization of a portion of this lactulose by dissolving it in water, evaporating to dryness, and treating with methanol as described above yielded a product having a m.p. of 168°–170° C. A mixed m.p. of this product with pure lactulose was 168°–171° C.

EXAMPLE 5

A sample containing 2.5 gm glucose, 0.89 gm boric acid and 100 ml water was adjusted to pH 11.0 with triethylamine and reacted for 3 hours at 70° C. Triethylamine and boric acid were then removed as in Example 1. HPLC analysis showed the product to be 48.0% fructose and 52.0% glucose.

EXAMPLE 6

A duplicate of the sample in Example 5 was treated the same except that the reaction time was 5 hours at 70° C. HPLC analysis showed the product to be 63.0% fructose and 37.0% glucose.

EXAMPLE 7

A sample containing 2.5 gm galactose, 0.89 gm boric acid and 100 ml water was adjusted to pH 11.0 with triethylamine, reacted for 3 hours at 70° C., and then treated as in Example 5. HPLC analysis showed the product to be 34.0% tagatose, 9.0% fructose, and 57.0% galactose.

EXAMPLE 8

A duplicate of the sample in Example 7 was treated the same except that the reaction time was 6 hours at 70° C. HPLC analysis showed the product to be 52.0% tagatose, 48.0% galactose, and a trace of fructose.

The process of this invention is unique because it is the first process for converting an aldose sugar to a ketose sugar that uses a tertiary and quaternary amine as an isomerizing reagent in the presence of the boric acid. The boric acid functions as a complexing reagent to prevent degradation and improve the yield of ketose. It is also the first chemical process to convert aldose sugars to ketose sugars in high yield in which the catalytic reagents can be completely recycled.

TABLE 1

| pH | Yield of Lactulose % | Monosaccharides % |
|---|---|---|
| 9.0 | 6 | <1 |
| 10.0 | 32 | 5 |
| 10.5 | 74 | 3 |
| 11.0 | 83 | 5 |

TABLE 2

| Amine | pH | Lactulose % | Monosaccharides % |
|---|---|---|---|
| 1,4-dimethyl-piperazine | 9.5 | 21 | <1 |
| N-Methyl-piperidine | 10.8 | 81 | <1 |
| N,N,N',N'-tetramethylethylenediamine | 9.7 | 33 | 5 |
| Triethylamine | 11.0 | 87 | 3 |

TABLE 3

| Sample | Cycle | pH | Lactulose % | Lactose % | Monosaccharides % |
|---|---|---|---|---|---|
| 1 | 1 | 11.0 | 52 | 48 | 0 |
|   | 2 | 10.95 | 73 | 14 | 13 |
| 2 | 1 | 11.0 | 87 | 9 | 4 |
|   | 2 | 10.6 | 65 | 20 | 4 |

I claim:

1. A process for producing ketose sugars in high yield comprising reacting an aldose sugar and boric acid in aqueous medium in the presence of a tertiary or quaternary amine, said boric acid and aldose sugar being present in a molar ratio of about one to one.

2. The process of claim 1 wherein the aldose sugar is present at a concentration of about 5.0 to 36.0% w/v, the boric acid concentration is about 0.89 to 6.4%, w/v, the amine is present in sufficient concentration to adjust the pH range of the aqueous reaction medium to about 9.0 to 11.0, and the temperature of the reaction is from about 38° C. to 70° C.

3. The process of claim 2 in which the aldose sugar is selected from the group consisting of lactose, glucose and galactose.

4. The process of claim 2 in which the amine is selected from the group consisting of triethylamine, 1,4-dimethylpiperazine, N-methyl-piperidine, N,N,N',N'-tetramethylethylenediamine, and N-benzyl, N,N,N-trimethylammonium methoxide.

5. A process for producing ketose sugars in high yield comprising reacting in aqueous medium at about 70° C. for about two to four hours, an aldose sugar and boric acid in the presence of sufficient triethylamine to adjust the pH of the aqueous reaction medium to between 9.0 and 11.0, evaporating the reacted sample to dryness and collecting the triethylamine-water distillate, treating the dried sample with anhydrous methanol to remove and reclaim the boric acid and to collect the first cycle yield of ketose sugar, mixing the reclaimed boric acid with the aforesaid triethylamine-water distillate, adding an aldose sugar, and reacting the aqueous mixture at about 70° C. for about two to four hours to obtan a second cycle yield of ketose sugar.

* * * * *